United States Patent
Lines et al.

(10) Patent No.: US 6,821,536 B2
(45) Date of Patent: Nov. 23, 2004

(54) ANTIOXIDATIVE COMPOSITIONS

(75) Inventors: Thomas Christian Lines, Hassel (LU); Mitsunori Ono, Lexington, MA (US)

(73) Assignee: Quercegen Holdings LLC, New Canaan, CT (US)

( * ) Notice: Subject to any disclaimer, the term of this patent is extended or adjusted under 35 U.S.C. 154(b) by 14 days.

(21) Appl. No.: 10/302,544

(22) Filed: Nov. 22, 2002

(65) Prior Publication Data

US 2004/0101595 A1 May 27, 2004

(51) Int. Cl.[7] .............. A23F 3/00; A23L 2/00
(52) U.S. Cl. .......... 426/73; 426/541; 426/549; 426/580; 426/590; 426/597
(58) Field of Search .......... 426/73, 597, 590, 426/580, 549

(56) References Cited

U.S. PATENT DOCUMENTS

| | | | |
|---|---|---|---|
| 6,261,589 B1 * | 7/2001 | Pearson et al. ............ | 424/439 |
| 6,277,426 B1 | 8/2001 | Reust | |
| 6,277,427 B1 * | 8/2001 | Husz ..................... | 426/590 |
| 6,299,925 B1 * | 10/2001 | Xiong et al. ............. | 426/597 |
| 6,579,544 B1 * | 6/2003 | Rosenberg et al. ........ | 424/736 |

OTHER PUBLICATIONS

Bors et al., "Flavanoids and Polyphenols: Chemistry and Biology", *Handbook of Antioxidants*, pp. 409–416 (1996).*

Crespy et al., "Quercetin, but not Its Glycosides, Is Absorbed from the Rat Stomach", *Journal of Agricultural and Food Chemistry*, vol. 50, pp. 68–621 (2002).*

Erlund et al., "Pharmacokinetics of quercetin from quercetin aglycone and rutin in healthy volunteers", *Eur. J. Clin. Pharmacol*, vol. 56, pp. 545–553 (2000).*

Guardia et al., "Anti–inflammatory properties of plant flavanoids. Effects of rutin, quercetin and hesperidin on adjuvant arthritis in rat", *Il Farmaco*, vol. 56, pp. 683–687 (2001).*

Saucier et al., "Synergetic Activity of Catechin and Other Antioxidants", *Journal of Agricultural and Food Chemistry*, vol. 47, No. 11, pp. 44914494 (Nov. 1999).*

Sesink et al., "Quercetin Glucuronides but Not Glucosides Are Present in Human Plasma after Consumption of Quercetin–3–Glucoside or Quercetin–4'–Glucoside[1]", *Human Nutrition and Metabolism Research Communication*, pp. 1938–1941 (2001).*

Thomas et al., "Ascorbate and Phenolic Antioxidant Interactions in Prevention of Liposomal Oxidation", *Lipids*, vol. 27, No. 7 (1992).*

Walle et al., "Quercetin Glucosides Are Completely Hydrolyzed in Ileostomy Patients before Absorption", *Human Nutrition and Metabolism Research Communication*, pp. 2658–1661 (2000).*

* cited by examiner

*Primary Examiner*—Helen Pratt
(74) *Attorney, Agent, or Firm*—Fish & Richardson P.C.

(57) ABSTRACT

This invention relates to a composition that contains quercetin, vitamin B1, vitamin B2, vitamin B3, vitamin B6, vitamin B12, vitamin C, caffeine, epigallocatechin gallate, epicatechin, epicatechin gallate, epigallocatechin, and polypheron E.

24 Claims, No Drawings

ANTIOXIDATIVE COMPOSITIONS

BACKGROUND

It is known that certain natural antioxidants, such as plant flavonoids, inhibit both acute and chronic phases of free-radical induced diseases. Further, some natural antioxidants exhibit synergy in their reactions with biologically relevant oxygen species, e.g., hydroxyl radicals, superoxides, oxysulfurs, sulfur dioxide, and nitrogen dioxide. For example, studies have shown synergistic antioxidative activities of vitamin C and phenolic antioxidants.

SUMMARY

This invention is based on the unexpected discovery that quercetin, an antioxidant, and a number of other natural products exhibit synergistic health benefits.

The invention features a composition that contains the following ingredients: vitamin B1, vitamin B2, vitamin B3, vitamin B6, vitamin B12, vitamin C, caffeine, quercetin, epigallocatechin gallate, epicatechin, epicatechin gallate, epigallocatechin, and polypheron E. This composition may also contain other ingredients, such as vitamin E, CoQ-10, soy isoflavones, taurine, sugar beet pectin fiber, and a ginko biloba extract. Further, the composition can be sweetened, if necessary, by adding a sweetener, e.g., sorbitol, maltitol, cane sugar, high fructose corn syrup, and the like. The composition can also contain amino acids, minerals, a flavor enhancer, or a coloring agent. It is known that the leaves of green tea contain epigallocatechin gallate, epicatechin, epicatechin gallate, epigallocatechin, and polypheron E. Thus, these five ingredients can be conveniently provided as a green tea extract.

The composition of the invention can be in dry form (e.g., powder or tablet) or in aqueous form (e.g., beverage or syrup). It can be a dietary supplement or a pharmaceutical formulation. It can also be a drink or a food product. Examples include tea (e.g., a tea drink and the contents of a tea bag), soft drinks, juice (e.g., a fruit extract and a juice drink), milk, coffee, cookies, cereals, chocolates, and snack bars. The composition, in any of the forms described above, can be used to treat arthritis, tumor, sexual dysfunction, chronic constipation, inflammatory bowel disease; improving concentration or mood; and lowering cholesterol levels or blood pressure. Also within the scope of this invention is a composition of the invention as an active agent, as well as use of the composition for the manufacture of a medicament, for treating the above-mentioned diseases.

The details of one or more embodiments of the invention are set forth in the accompanying description below. Other features, objects, and advantages of the invention will be apparent from the description and from the claims.

DETAILED DESCRIPTION

A composition of this invention contains vitamin B1, vitamin B2, vitamin B3, vitamin B6, vitamin B12, vitamin C, caffeine, quercetin, epigallocatechin gallate, epicatechin, epicatechin gallate, epigallocatechin, and polypheron E. A green tea extract can be conveniently used to provide epigallocatechin gallate, epicatechin, epicatechin gallate, epigallocatechin, and polypheron E.

Exemplary quantities of the ingredients of this composition are: 0.1–50 mg of vitamin B1, 0.1–150 mg of vitamin B2, 0.1–2000 mg of vitamin B3, 0.1–200 mg of vitamin B6, 5–150 $\mu$g of vitamin B12, 50–2000 mg of vitamin C, 50–1500 mg of caffeine, 20–2000 mg of quercetin, 10–500 mg of epigallocatechin gallate, 10–500 mg of epicatechin, 10–500 mg of epicatechin gallate, 10–500 mg of epigallocatechin, and 10–500 mg of polypheron E, which can be dissolved or dispersed in a 1 L aqueous solution. The quantities of the ingredients can also be those of the same relative ratio to those listed above. The term "quercetin" refers to both quercetin aglycon and quercetin derivatives, e.g., quercetin-3-O-glucoside, quercetin-5-O-glucoside, quercetin-7-O-glucoside, quercetin-9-O-glucoside, quercetin-3-O-rutinoside, quercetin-3-O-[$\alpha$-rhamnosyl-(1→2)-$\alpha$-rhamnosyl-(1→6)]-$\beta$-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon, an active form absorbed in the body. The quantity of quercetin mentioned above refers to that of quercetin aglycon or the quercetin moiety of a quercetin derivative. As an example, a composition for daily use can be a 1 L aqueous solution containing 1000 mg of quercetin, 30 mg of vitamin B1, 85 mg of vitamin B2, 1 g of vitamin B3, 100 mg of vitamin B6, 120 $\mu$g of vitamin B12, 1200 mg of vitamin C, 1000 IU of vitamin E, 1000 mg of caffeine, and a green tea extract containing 120 mg of epigallocatechin gallate, 140 mg of epicatechin, 360 mg of epicatechin gallate, 360 mg of epigallocatechin, and 120 mg of polypheron E.

This composition may also contain one or more other active ingredients, such as vitamin E, CoQ-10, soy isoflavones, taurine, sugar beet pectin fiber, and a ginko biloba extract. Exemplary quantities of these ingredients are: 3–1000 IU of vitamin E, 10–400 mg of CoQ-10, 20–600 mg of soy isoflavones, 10–1000 mg of taurine, 1–15 g of sugar beet pectin fiber, and 50–500 mg of a ginko biloba extract (dry weight). Further, the composition can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose.

An example of the above-described composition is a powder. It can be used conveniently to prepare beverages, e.g., tea or juice. The powder can also be used to prepare paste, jelly, capsules, or tablets. Lactose and corn starch are commonly used as diluents for capsules and as carriers for tablets. Lubricating agents, such as magnesium stearate, are typically added to form tablets.

The composition of this invention can also be a dietary supplement or a pharmaceutical formulation. As a dietary supplement, additional nutrients, such as minerals or amino acids may be included. The composition can also be a drink or a food product, e.g., tea, soft drinks, juice, milk, coffee, cookies, cereals, chocolates, and snack bars.

The composition, in any of the forms described above, can be used for treating diseases or disorders, such as arthritis, tumor, sexual dysfunction, chronic constipation, inflammatory bowel disease; improving concentration or mood; and lowering cholesterol levels or blood pressure.

The term "tumor" refers to benign tumor, as well as malignant tumor (e.g., leukemia, colon cancer, kidney cancer, liver cancer, breast cancer, or lung cancer). The terms "treating", "improving", and "lowering" refer to the administration of an effective amount of a composition of the invention to a subject, who has one or more of the just-mentioned diseases or disorders, or a symptom or a predisposition of one of more of them, with the purpose to cure, alleviate, relieve, remedy, or ameliorate one or more of the diseases or disorders, or the symptoms or the predispositions of one or more of them. The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. The term "effective amount" refers to a dose of the composition that is sufficient to provide a therapeutic benefit, e.g., lowering cholesterol levels or blood pressure. Both in vivo and in vitro studies can be conducted to determine optimal administration routes and doses.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Formulation 1 was prepared as follows. To 30 mL purified water were added: vitamin B1 (8 mg), vitamin B2 (21.1 mg), vitamin B3 (248 mg), vitamin B6 (24.8 mg), vitamin B12 (20.4 mg), vitamin C (74.4 mg), vitamin E (37.2 IU), caffeine (99.2 mg), quercetin aglycon (248 mg), and a green tea extract containing epigallocatechin gallate (80 mg), epicatechin (80 mg), epicatechin gallate (80 mg), epigallocatechin (80 mg), and polypheron E (80 mg) at room temperature. All ingredients can be obtained from Spectrum Laboratory Products, Inc., Gardena, Calif.; Sigma, St. Louis, Mo.; and Aldrich, Milwaukee, Wis. The above mixture was vigorously stirred by using a food mixer and then diluted up to 150 mL with purified water.

In one experiment, male Spregue-Dawley rats (150–180 gram; Charles River Lab, Boston, Mass.) were kept in filter-topped cages with free access to food and water, and housed in a positive pressure room with controlled temperature and photoperiod during studies. As an animal model for inflammatory bowel disease (e.g., Crohn's disease), colitis (colon growth caused by inflammation) was induced by intracolonic instillation of 25 mg of a hapten reagent, 2,4-dinitrobenzenesulfonic acid (TCI, Japan), in 0.5 ml of 30% vol/vol ethanol. Each rat was first anaesthetized with metafane and then DNBS/ethanol was injected into the colon, 8 cm proximal to the anus, with a PE 50 cannula. 2 ml of air was then gently injected through the cannula to ensure that the solution remained in the colon. The rat was then kept in a vertical position for 30 second and returned to its cage. By using the same procedures, rats in the blank-control group received 0.5 ml of 30% ethanol. See Hogaboam, et al., Eur. J. Pharmacol. (1996) 309:261–269.

Fomulation 1 and a quercetin aglycon solution, in which methylcellulose (MC) was added to reach a final concentration of 1%, were respectively fed to the rats orally once a day for 7 days. Each daily dose contained 3.125 mg to 25 mg of quercetin aglycon for each kilogram of body weight. The weight of each rat was monitored every 24 hours. At day 7, rats were killed and their colon were removed and weighed. Before removal of each colon, the presence or absence of adhesions between the colon and other organs were recorded upon opening the abdominal cavity. The colon-to-body weight ratio was then calculated for each animal. The net increase in ratio of the vehicle-control group relative to the blank-control group was used as a base value for comparison with the treated groups. Both formulation 1 and quercetin aglycon inhibited colon growth at the dosage of 25 mg/kg and failed to do so at the dosage of 3.125 mg/kg. However, at 6.25 mg/kg and 12.5 mg/kg, formulation 1 was much more efficacious than quercetin aglycon in inhibiting colon growth.

In another experiment, a 10 mg/mL bacterial suspension was prepared by suspending ground, heat-killed *Mycobacterium tuberculosis* H37Ra in incomplete Freund's adjuvant. Adjuvant arthritis (AA) was then induced in female Lewis rats by an intracutaneous injection into the base of the tail with 0.1 ml of the above suspension. The rats were then orally given formulation 1 or a quercetin aglycon solution (1% MC) once a day for 12 days at a daily dose of 25 mg/kg quercetin aglycon, starting the day following the induction. The development of polyarthritis was monitored daily by macroscopic inspection and assignment of an arthritis index to each animal, during the critical period (from day 10 to day 25 after immunization). The intensity of polyarthritis was scored according to the following scheme: (a) Grades for each paw range from 0 to 3 based on erythema, swelling, and deformity of the joints, i.e., 0 for no erythema or swelling; 0.5 if swelling is detectable in at least one joint; 1 for mild swelling and erythema; 2 for swelling and erythema of both tarsus and carpus; and 3 for ankylosis and bone deformity. (b) Grades for other body parts: 0.5 for redness and another 0.5 for knots in each ear; 1 for connective tissue swelling in the nose; and 1 for knots or kinks in the tail. See Schorlemmer et al., Drugs Exptl. Clin. Res. (1991) 17:471–483. Compared with the rats treated with quercetin aglycon, those treated with formulation 1 showed much more significant amelioration in arthritis symptoms at day 18.

In still another experiment, female BD2F1 (C57BL/6× DBA/2 F1) rats were first obtained from Charles River Lab. The rats were supplied with food and water adlibitum. As an animal model for cancer, 50,000 cells of p388 leukemia were inoculated intraperitoneally into 7 week old female BD2F1 rats at day 0. Formulation 1 or a quercetin aglycon solution (1% MC) was administered orally once a day for 14 days at a daily dose of 12.5 mg/kg quercetin aglycon. All rats in the control group, but not those in the treated groups, died around day 21 as a result of ascites. The anti-cancer activity was determined by comparing the mean survival time of the treated group with that of the control group. See Yoshimatsu et al., Cancer Res. (1997) 57:3208–3213. Rats treated with formulation 1 showed a substantial longer mean survival time than those treated with quercetin aglycon.

Phosphodiesterase-5 (PDE-5) is an enzyme involved in sexual function. In a further experiment, PDE-5 activity was determined according to a well-known method with some modifications. See Thompson et al., Methods Enzymol. (1974) 38:205–212. Activity of purified PDE-5 was measured in a reaction mixture of pH 7.5 containing 8 µM cGMP (64 µCi/ml of [$^3$H]-cGMP), 40 mM MOPS, 0.5 mM EGTA, 15 mM magnesium acetate, and 0.15 mg/ml BSA in the presence of formulation 1, a quercetin aglycon solution, and a 3-isobutyl-1-methylxanthine (IBMX, a general PDE-5 inhibitor) solution (1% MC) at various concentrations ranging from 1 µM to 100 µM. The reaction was performed at 37° C. for 60 min, and terminated by heating at 70° C. for 2 min. The labeled enzymatic reaction product [$^3$H]-GMP was then degraded into [$^3$H]-guanosine and phosphate in the presence of 0.1 units of nucleotidase. Finally, undegraded [$^3$H]-cGMP was absorbed onto anion exchange resin. [$^3$H]-Guanosine in the supernatant was counted for radioactivity in a liquid scintillation counter. It was found that formulation 1 inhibited PDE-5 activities in a dose-dependent manner with an IC50 value much lower than those of quercetin aglycon and IBMX.

Human studies were also conducted to evaluate two other compositions of this invention, i.e., formulations 2 and 3. Formulation 2 was prepared as follows. To 200 mL purified water were added: vitamin B1 (30 mg), vitamin B2 (85 mg), vitamin B3 (1 g), vitamin B6 (100 mg), vitamin B12 (120 µg), vitamin C (1200 mg), vitamin E (1000 IU), caffeine (1000 mg), quercetin aglycon (1000 mg), and a green tea extract containing epigallocatechin gallate (120 mg), epicatechin (140 mg), epicatechin gallate (360 mg), epigallocatechin (360 mg), and polypheron E (120 mg) at room temperature. The mixture was vigorously stirred by using a food mixer and then diluted up to 1 L with purified water. Formulation 3 was prepared as follows. To 200 mL purified water were added: vitamin B1 (3.75 mg), vitamin B2 (4.25 mg), vitamin B3 (50 mg), vitamin B6 (5 mg), vitamin B12 (15 µg), vitamin C (150 mg), vitamin E (7.5 IU) and caffeine (200 mg), quercetin aglycon (50 mg), and a green tea extract containing epigallocatechin gallate (30 mg), epicatechin (35 mg), epicatechin gallate (90 mg), epigallocatechin (90 mg), and polypheron E (30 mg) at room temperature. The above mixture was vigorously stirred by using a food mixer. The mixture was then diluted up to 1 L with purified water and orange juice so that the final solution contained 10% by weight orange juice.

In one study, four male subjects and four female subjects suffering from high cholesterol levels and high blood pressure were treated with formulation 2. Each of the subjects drank 1 bottle of formulation 2 (20 fl. oz., or 591 mL) daily for 10 days. Then, half of the group (one male subject and 3 female subjects) continued to drink 1 bottle of the same formulation daily for another 20 days. The other half of the group stopped this regimen for 5 days and then started drinking 2 bottles of the same formulation daily for 20 days. It was found that all subjects had improved concentration and mood. Their cholesterol levels and blood pressure were down to normal range. No significant weight losses were observed among the subjects. Two subjects in each of the two half groups felt thirsty during this study.

In another study, two male subjects and two female subjects drank 2 bottles of formulation 2 (20 fl. oz. each bottle) daily for one month. It was found that all subjects had improved mood and sex drive. All subjects experienced weight losses ranging from 10–25 pounds (2–6% body weight). After termination of this regimen, most subjects had mood swings.

In still another study, one male subject and three female subjects suffering from serious constipation were treated with formulation 3. Each drank 1–3 bottles of formulation 3 (20 fl. oz. each bottle) daily for 1 week. Constipation was relieved for all subjects.

In yet another study, a male subject, who suffered from Crohn's disease and had symptoms of stomach ache and diarrhea, was also treated with formulation 3. The subject drank 2 bottles of formulation 3 (20 fl. oz. each bottle) daily for 1 week. Both symptoms were dramatically reduced and the effects were sustained for at least one week after termination of the regimen.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition comprising vitamin B1, vitamin B2, vitamin B3, vitamin B6, vitamin B12, vitamin C, caffeine, quercetin, epigallocatechin gallate, epicatechin, epicatechin gallate, epigallocatechin, and polypheron E.

2. The composition of claim 1, further comprising vitamin E.

3. The composition of claim 2, further comprising CoQ-10, soy isoflavones, taurine, sugar beet pectin fiber, or a ginko biloba extract.

4. The composition of claim 3, wherein the composition is in dry form.

5. The composition of claim 3, wherein the composition is tea, soft drinks, juice, milk, coffee, cookies, cereals, chocolates, or snack bars.

6. The composition of claim 2, wherein the composition is in dry form.

7. The composition of claim 2, wherein the composition is tea, soft drinks, juice, milk, coffee, cookies, cereals, chocolates, or snack bars. isoflavones, taurine, sugar beet pectin fiber, or a ginko biloba extract.

8. The composition of claim 1, further comprising CoQ-10, soy isoflavones, taurine, sugar beet pectin fiber, or a ginko biloba extract.

9. The composition of claim 8, wherein the composition is in dry form.

10. The composition of claim 8, wherein the composition is tea, soft drinks, juice, milk, coffee, cookies, cereals, chocolates, or snack bars.

11. The composition of claim 1, wherein the composition is in dry form.

12. The composition of claim 1, wherein the composition is tea, soft drinks, juice, milk, coffee, cookies, cereals, chocolates, or snack bars.

13. A composition comprising vitamin B1, vitamin B2, vitamin B3, vitamin B6, vitamin B12, vitamin C, caffeine, quercetin, and a green tea extract containing epigallocatechin gallate, epicatechin, epicatechin gallate, epigallocatechin, and polypheron E.

14. The composition of claim 13, further comprising vitamin E.

15. The composition of claim 14, further comprising CoQ-10, soy isoflavones, taurine, sugar beet pectin fiber, or a ginko biloba extract.

16. The composition of claim 15, wherein the composition is in dry form.

17. The composition of claim 15, wherein the composition is tea, soft drinks, juice, milk, coffee, cookies, cereals, chocolates, or snack bars.

18. The composition of claim 14, wherein the composition is in dry form.

19. The composition of claim 14, wherein the composition is tea, soft drinks, juice, milk, coffee, cookies, cereals, chocolates, or snack bars.

20. The composition of claim 13, further comprising CoQ-10, soy isoflavones, taurine, sugar beet pectin fiber, or a ginko biloba extract.

21. The composition of claim 20, wherein the composition is in dry form.

22. The composition of claim 20, wherein the composition is tea, soft drinks, juice, milk, coffee, cookies, cereals, chocolates, or snack bars.

23. The composition of claim 13, wherein the composition is in dry form.

24. The composition of claim 13, wherein the composition is tea, soft drinks, juice, milk, coffee, cookies, cereals, chocolates, or snack bars.

* * * * *